(12) United States Patent
Ribeiro et al.

(10) Patent No.: US 9,018,426 B1
(45) Date of Patent: Apr. 28, 2015

(54) PROCESSES FOR PRODUCING MULTI-CARBON ALCOHOLS

(71) Applicant: Celanese International Corporation, Irving, TX (US)

(72) Inventors: Claudio Ribeiro, Houston, TX (US); Andrew Shuff, Flower Mound, TX (US); Tianshu Pan, Charlotte, NC (US)

(73) Assignee: Celanese International Corporation, Irving, TX (US)

( * ) Notice: Subject to any disclaimer, the term of this patent is extended or adjusted under 35 U.S.C. 154(b) by 0 days.

(21) Appl. No.: 14/134,333

(22) Filed: Dec. 19, 2013

(51) Int. Cl.
C07C 27/04 (2006.01)
C07C 27/26 (2006.01)
C07C 29/74 (2006.01)
C07C 29/82 (2006.01)
C07C 29/32 (2006.01)

(52) U.S. Cl.
CPC ............... *C07C 29/82* (2013.01); *C07C 29/32* (2013.01)

(58) Field of Classification Search
USPC ............................................ 568/902.12, 913
See application file for complete search history.

(56) References Cited

U.S. PATENT DOCUMENTS

| | | | |
|---|---|---|---|
| 2,762,847 A | 9/1956 | Miller et al. | |
| 3,864,407 A | 2/1975 | Yates | |
| 4,011,273 A | 3/1977 | Abend et al. | |
| 4,533,775 A | 8/1985 | Fox et al. | |
| 4,551,444 A | 11/1985 | Lin et al. | |
| 5,095,156 A | 3/1992 | Radlowski et al. | |
| 5,159,125 A | 10/1992 | Hagen | |
| 5,300,695 A | 4/1994 | Radlowski | |
| 5,849,662 A | 12/1998 | Praserthdam | |
| 6,166,265 A | 12/2000 | Kanand et al. | |
| 6,218,326 B1 | 4/2001 | Datta et al. | |
| 6,323,383 B1 | 11/2001 | Tsuchida et al. | |
| 7,700,810 B2 | 4/2010 | Kourtakis et al. | |
| 7,700,811 B2 | 4/2010 | Kourtakis et al. | |
| 7,700,812 B2 | 4/2010 | Kourtakis et al. | |
| 7,700,813 B2 | 4/2010 | Kourtakis et al. | |
| 7,705,192 B2 | 4/2010 | Kourtakis et al. | |
| 7,807,857 B2 | 10/2010 | Kourtakis et al. | |
| 7,915,196 B2 | 3/2011 | Parent et al. | |
| 8,071,822 B2 | 12/2011 | Ozer et al. | |
| 8,071,823 B2 | 12/2011 | Ozer et al. | |
| 8,232,433 B2 | 7/2012 | Onda et al. | |
| 8,569,203 B2 | 10/2013 | Weiner et al. | |
| 2007/0255079 A1 | 11/2007 | Tsuchida et al. | |
| 2009/0056204 A1 | 3/2009 | Tsuchida et al. | |
| 2010/0160692 A1 | 6/2010 | Kourtakis et al. | |
| 2010/0185021 A1 | 7/2010 | Ross et al. | |
| 2010/0205857 A1 | 8/2010 | Dijk et al. | |
| 2010/0298613 A1 | 11/2010 | Tanaka et al. | |
| 2011/0257443 A1 | 10/2011 | Weiner et al. | |
| 2011/0288344 A1 | 11/2011 | Grady et al. | |
| 2012/0040427 A1 | 2/2012 | Bell et al. | |
| 2013/0131399 A1 | 5/2013 | Weiner et al. | |
| 2013/0165700 A1 | 6/2013 | Zhou et al. | |
| 2013/0165701 A1 | 6/2013 | Zhou et al. | |
| 2013/0165703 A1 | 6/2013 | Weiner et al. | |
| 2013/0178662 A1 | 7/2013 | Zhou et al. | |
| 2013/0178666 A1 | 7/2013 | Zhou et al. | |
| 2013/0178668 A1 | 7/2013 | Zhou et al. | |
| 2013/0178669 A1 | 7/2013 | Zhou et al. | |
| 2013/0184502 A1 | 7/2013 | Zhou et al. | |
| 2013/0211150 A1 | 8/2013 | Zhou et al. | |
| 2013/0225878 A1 | 8/2013 | Weiner et al. | |
| 2013/0245332 A1 | 9/2013 | Weiner et al. | |

FOREIGN PATENT DOCUMENTS

| | | |
|---|---|---|
| CN | 1528727 | 9/2004 |
| CN | 101530802 | 9/2009 |
| WO | WO 2006/059729 | 6/2006 |
| WO | WO 2009/097310 | 8/2009 |
| WO | WO 2009/097312 | 9/2009 |

OTHER PUBLICATIONS

OXO Alcohols, Process Economics Program Report 21E, Sep. 2010 (203 pages).
Diaz, et al., J. of Catalysis (2003), 215, pp. 220-233.
Matsu-ura, et al., Journal of Organic Chemistry, vol. 71, No. 21, pp. 8306-8308, (2006).
Dvornikoff, et al., Journal of Organic Chemistry, 1957, 11, pp. 540-542.
Carlini, et al., Journal of Molecular Catalysis A: Chemical, vol. 212, 2004, pp. 65-70.
DiCosimo, et al., Journal of Catalysis, vol. 190, 2000, pp. 261-275.

*Primary Examiner* — Sikarl Witherspoon

(57) ABSTRACT

In one embodiment, the invention is to a process for producing multi-carbon alcohols, including butanol and/or hexanol. The process comprises the step of reacting ethanol in a reactor to form a crude product comprising butanol, ethanol, and water. The process further comprises the step of separating at least a portion of the crude product in a first distillation zone to form a first distillate comprising ethanol and a first residue comprising butanol, and water. The process further comprises the step of separating at least a portion of the first residue in a second distillation zone to form a second distillate and a second residue comprising butanol.

20 Claims, 3 Drawing Sheets

PROCESSES FOR PRODUCING MULTI-CARBON ALCOHOLS

FIELD OF THE INVENTION

The present invention relates generally to the production of multi-carbon alcohols, such as butanol and hexanol. More specifically, the present invention relates to the production of multi-carbon alcohols via the condensation of ethanol over catalyst and to separation schemes for purifying these multi-carbon alcohols.

BACKGROUND OF THE INVENTION

Many studies have been performed in the hopes of developing an economically viable process for producing multi-carbon alcohols, such as butanol and hexanol. Because these multi-carbon alcohols may be used as fuel or fuel additives in an internal combustion engine, the multi-carbon alcohols present a possible solution to the problem of worldwide dependency on oil. In some cases, butanol and hexanol may present a better fuel option than ethanol because these compounds are more similar to gasoline than ethanol, e.g., similar longer hydrocarbon chains and non-polar characteristics. In addition to being used in fuel applications, butanol may also be used in the manufacture of pharmaceuticals, polymers, pyroxylin plastics, herbicide esters, and butyl xanthate. Butanol and/or hexanol may also be used as solvents for the extraction of essential oils; as an ingredient in perfumes; as an extractant in the manufacture of antibiotics, hormones, and vitamins; as a solvent for paints, coatings, natural resins, gums, synthetic resins, alkaloids, and camphor; as a softener; as a swelling agent in textiles; as a component of brake fluids, cleaning formulations, degreasers, and repellents; and as a component of ore floatation agents and of wood-treating systems.

Butanol is typically produced by reacting petrochemical feedstock propylene in the presence of a rhodium-based homogeneous catalyst. In this process, propylene is hydroformylated to butyraldehyde, which is then hydrogenated to produce butanol. The cost of producing butanol using this method, however, has become unpredictable due to the fluctuating natural gas and crude oil prices.

Butanol may also be produced via the condensation of ethanol over a basic catalyst at high temperature using the Guerbet reaction. The reaction mechanism of the Guerbet reaction may comprise the sequence shown in Reaction Scheme 1. Two ethanol molecules are oxidized to the respective intermediate aldehydes. Two of the aldehydes undergo an aldol condensation reaction to form crotonaldehyde, which is then reduced to butanol via hydrogenation.

Reaction Scheme 1

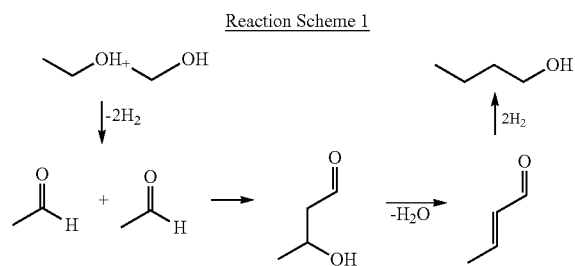

Hexanol is typically produced via the oligomerization of ethylene using triethylaluminium followed by oxidation of alkylaluminium products. This process, however, presents significant safety hazards due to the high reactivity of triethylaluminum.

Although various reaction schemes may be known, there has been little, if any, disclosure relating to separation schemes that may be employed to effectively separate the multi-carbon alcohols, e.g., butanol and/or hexanol, from the crude reaction product formed via the various reaction schemes. Thus, the need exists for separation schemes capable of effectively yielding a purified multi-carbon alcohol product from the crude reaction product(s).

The references mentioned above are hereby incorporated by reference.

BRIEF DESCRIPTION OF DRAWINGS

The invention is described in detail below with reference to the appended drawings, wherein like numerals designate similar parts.

SUMMARY OF THE INVENTION

Figure 1:
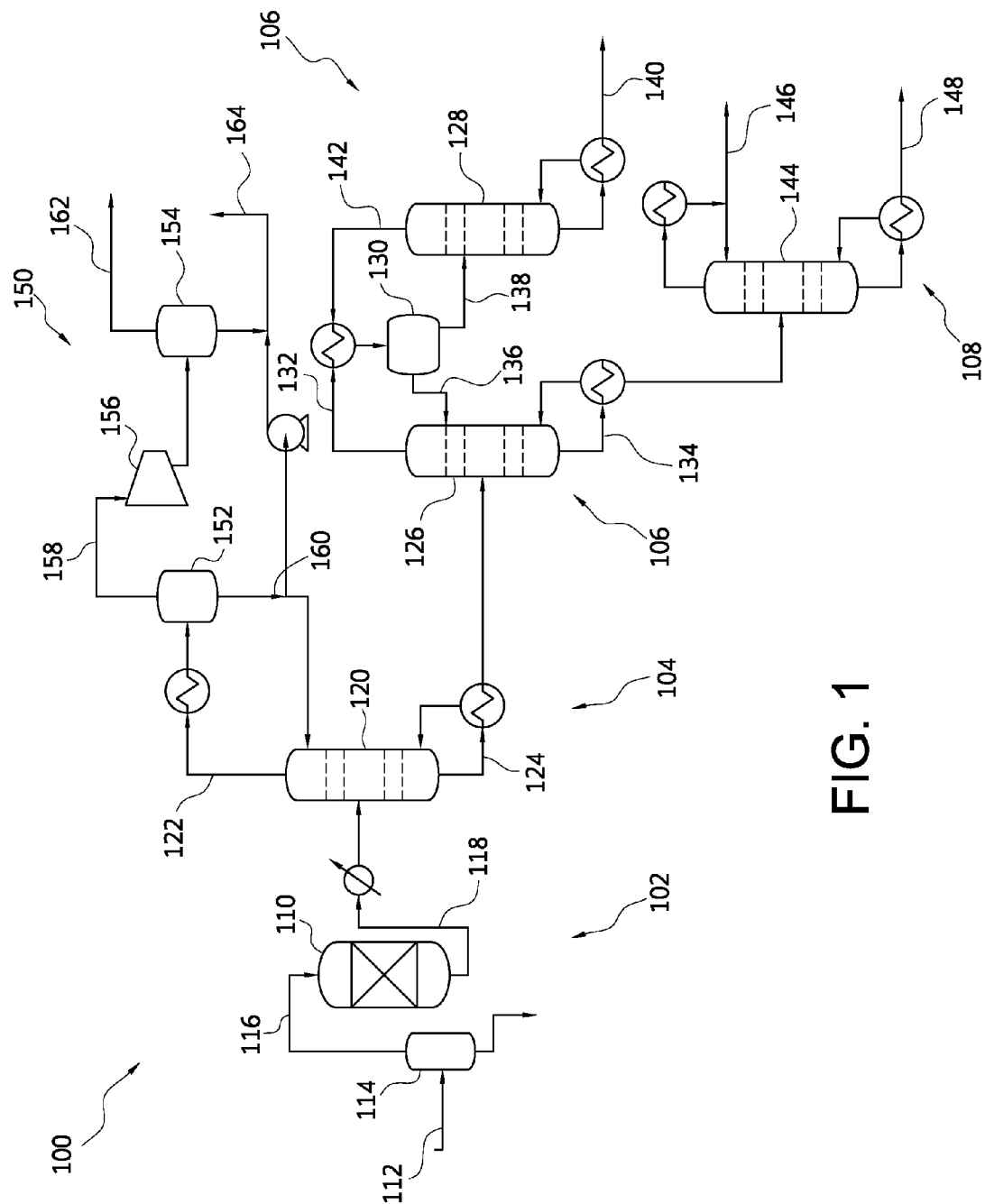
FIG. 1 is a schematic diagram of a multi-carbon alcohols separation system in accordance with one embodiment of the present invention.

In a first embodiment, the present invention is directed to a process for producing multi-carbon alcohols, e.g., butanol and/or hexanol. The process comprises the step of reacting ethanol (from an ethanol feed stream) in a reactor to form a crude product comprising butanol, ethanol, and water. The crude product may further comprise hexanol. In one embodiment, the crude product is substantially free of methanol, propanol, pentanol, or isotopes thereof and/or the crude product is substantially free of esters of butanol, ethanol, hexanol, methanol, pentanol, or octanol. The crude product may comprise from 0.1 wt. % to 60 wt. % ethanol; from 15 wt. % to 80 wt. % butanol; from 1 wt. % to 30 wt. % water; and/or from 0.1 wt. % to 30 wt. % hexanol. The crude product may comprise, by weight, more ethanol than butanol.

The process further comprises the step of separating at least a portion of the crude product in a first distillation zone to form a first distillate comprising ethanol and a first residue comprising butanol and water (and optionally hexanol). The first distillate may optionally comprise one or more light ends compound selected from the group consisting of acetaldehyde, ethylene, butyraldehyde, and diethyl ether. In one embodiment, the crude product is fed to the first distillation zone as a liquid or as a mixture of liquid and vapor. Preferably, the first distillation zone comprises at least one column operated above 10 psig and/or at a temperature above 90° C. The process further comprises the step of separating at least a portion of the first residue in a second distillation zone to form a second distillate and a second residue comprising butanol and optionally hexanol. Preferably the second distillation zone comprises at least two columns and each of the at least two columns forms a distillate comprising from 30 wt. % to 70 wt. % butanol and from 30 wt. % to 70 wt. % water. In one embodiment, the first of the at least two distillation columns operates at a top pressure lower than the top pressure of the second of the at least two distillation columns. The process optionally comprises the step of separating at least a portion of the second residue in a third distillation zone to form a third distillate comprising butanol and a third residue comprising hexanol. The process may further comprise the steps of condensing at least a portion of the first distillate to form a condensed first distillate (comprising ethanol); and/or removing a vent stream comprising the one or more light ends compounds; and/or feeding to the reactor the condensed first distillate. The condensed first distillate may comprise greater than 70 wt. % ethanol and/or from 0.001 wt. % to 2 wt. % butanol and the first residue may comprise less than 0.5 wt. % ethanol. The first residue may be substantially free of one or more light ends compounds selected from the group consisting of acetaldehyde, ethylene, butyraldehyde, and diethyl ether. The second residue may comprise less than 1 wt. % water and/or the third distillate may comprise from 95 wt. % to 99.99 wt. % butanol, from 0.01 to 3 wt. % hexanol, and/or from 0.01 wt. % to 1 wt. % water. The third distillate may comprise, by weight, more hexanol than water. The process may further comprise the step of forming from the first residue a heterogeneous azeotrope comprising more than one liquid phase.

DETAILED DESCRIPTION OF THE INVENTION

Introduction

The present invention generally relates to processes for purifying a reaction mixture of multi-carbon alcohols from crude reaction product. The multi-carbon alcohols may be linear multi-carbon alcohols.

Multi-carbon alcohols, e.g., butanol and hexanol, may be produced via conventional processes. For example, butanol may be produced via the Guerbet condensation reaction, and hexanol may be produced via the oligomerization of ethylene using triethylaluminum followed by oxidation of the alkylaluminum products.

In the Guerbet condensation reaction, ethanol may be used as the starting material to produce butanol. The Guerbet reaction utilizes two separate catalysts, a basic catalyst and a hydrogenation catalyst.

The process described herein may utilize a catalyst different from those of the Guerbet reaction. As such, a unique crude product may be formed. For example, a crude product comprising butanol, hexanol, and/or light components may be formed. It has now been found that hexanol may also be formed via the side reactions. For example, hexanol may be formed via the addition of aldehyde to butyraldehyde, which is a butanol intermediate. In addition, reaction intermediates can form competing by-products, which may lead to unwanted impurities in the crude multi-carbon alcohol product. For example, diethyl ether and ethylene may be formed due to the dehydration of ethanol in the presence of an acidic catalyst. Butyraldehyde may also react with other intermediates to form 2-ethylbutanol and 2-ethylhexanol. It is generally known that these impurities add problems and uncertainty to a separation scheme that may be employed to recover the purified multi-carbon alcohols.

Although some reaction schemes for producing multi-carbon alcohols are known, e.g., the Guerbet reaction, there has been little, if any, disclosure relating to separation schemes that may be employed to effectively separate the multi-carbon alcohols, e.g., butanol and/or hexanol, from the crude reaction product formed via the various reaction schemes. Also, there is little, if any, disclosure relating to separation schemes that may be employed to separate unique crude products formed by single catalyst reactions, as discussed herein. Conventional separation schemes and techniques have not addressed the problems and unpredictability that accompany crude multi-carbon alcohol products that have these types of impurity content. Importantly, the effects of the various by-products and azeotropes that may be formed have not been explored. For example, without being bound by theory, it is believed that separation problems may arise because the unique crude reactor product contains impurities that are both lighter and heavier than the target product (n-butanol and/or hexanol). In addition, many of the components in the crude reactor product, e.g., ethanol, butanol, and hexanol, may form an azeotrope with water, thus resulting in additional separation issues. Also, some of the light components present in the crude product may also form an azeotrope, e.g., diethyl ether and acetaldehyde. Further, some of the reaction intermediates, e.g., butyraldehyde, have boiling points that are very similar to that of ethanol, thus creating additional separation problems.

The inventors have now found that the unique crude multi-carbon alcohol product may be effectively separated using the processes disclosed herein to yield a purified multi-carbon alcohol. Without being bound by theory, it is believed that the removal of ethanol from the crude product (in the first separation step) provides for the subsequent formation of a heterogeneous (two phase) butanol-water azeotrope, which, when separated, effectively yields an anhydrous multi-carbon alcohol final product. The initial removal of ethanol leads to the formation of an aqueous butanol-water azeotrope phase and an organic butanol-water azeotrope phase. In one embodiment, the aqueous butanol-water phase comprises more water than butanol and/or the organic butanol-water azeotrope comprises more butanol than water. For example, the aqueous butanol-water phase may comprise greater than 50 wt. % water, e.g., greater than 60 wt. %, greater than 75 wt. %, greater than 85 wt. %, greater than 90 wt. %, greater than 95 wt. % or greater than 99 wt. %; and less than 50 wt. % butanol, e.g., less than 40 wt. %, less than 25 wt. %, less than 20 wt. %, less than 10 wt. %, less than 5 wt. %, or less than 1 wt %, wherein the weight percentages are based on the total weight of the aqueous phase. The organic butanol-water phase may comprise greater than 50 wt. % butanol, e.g., greater than 60 wt. %, greater than 75 wt. %, greater than 85 wt. %, greater than 90 wt. %, greater than 95 wt. % or greater than 99 wt. %; and less than 50 wt. % water, e.g., less than 40 wt. %, less than 25 wt. %, less than 20 wt. %, less than 10 wt. %, less than 5 wt. %, or less than 1 wt %, wherein the weight percentages are based on the total weight of the organic phase. In one embodiment, if the butanol-water mixture remains heterogeneous, the effective separation of the butanol-water aqueous and organic phases into the respective individual components may, beneficially, be achieved via simple distillation.

It has been found that, when ethanol is not separated from the crude multi-carbon alcohol product, the two-phase region of butanol-water system is not formed. Instead, a single-phase, homogeneous ethanol-butanol-water mixture may be produced. Such a mixture has been found to be much more difficult to effectively separate, as compared to the aqueous butanol-water phase and the organic butanol-water phase. Without the initial removal of ethanol and the formation of the two-phase butanol/water azeotrope, an anhydrous alcohol product cannot be obtained from the crude product (comprising butanol, ethanol, and water with simple distillation, and additional separation units would be required, e.g., membranes or PSAs.

In addition, the inventors have found that the separation of ethanol from the crude product (in the first separation step) allows the light by-products to be effectively removed with only a single vaporization step. If ethanol is not first separated from the crude product, the separation of the light by-products requires multiple vaporization steps, which increases energy consumption. Also, in some cases, by operating the first tower at an elevated pressure, ethanol separation and/or recovery may be improved, e.g., less ethanol is lost via a vent stream. For example, the elevated pressure may allow the subsequent condensation step to be performed at higher temperatures, which reduces the need for costly cooling, e.g., refrigeration.

In one embodiment, the present invention relates to a process for producing multi-carbon alcohols, e.g., butanol or hexanol. The process comprises the step of reacting ethanol (optionally from an ethanol feed and in a reactor) to form a crude multi-carbon alcohol product. In one embodiment, the crude multi-carbon alcohol product comprises butanol. In one embodiment, the crude multi-carbon alcohol product comprises butanol and hexanol, and optionally ethanol and/or water. The ethanol may be unreacted ethanol. The water may be the by-product of the condensation reaction. In a preferred embodiment, the crude multi-carbon alcohol product comprises butanol, hexanol, ethanol and water. Preferably, the multi-carbon alcohols are linear multi-carbon alcohols. As such, butanol may refer to and include n-butanol and hexanol may refer to and include n-hexanol.

In one embodiment, the crude multi-carbon alcohol product stream may comprise from 15 to 80 wt. % butanol, e.g., from 15 to 70 wt. %, or from 20 to 75 wt. %. In terms of lower limits, the crude multi-carbon alcohol product may comprise at least 15 wt. % butanol, e.g., at least 20 wt. %, or at least 25 wt. %. In terms of upper limits, the crude multi-carbon alcohol product may comprise at most 80 wt. % butanol, e.g., at most 70 wt. %, or at most 60 wt. %.

In one embodiment, the crude multi-carbon alcohol product may comprise from 0.1 to 30 wt. % hexanol, e.g., from 2 to 20 wt. %, or from 5 to 10 wt. %. In terms of lower limits, the crude multi-carbon alcohol product may comprise at least 0.1 wt. % hexanol, e.g., at least 2 wt. % or at least 5 wt. %. In terms of upper limits, the crude multi-carbon alcohol product may comprise at most 30 wt. % hexanol, e.g., at most 20 wt. %, or at most 10 wt. %.

In one embodiment, the crude multi-carbon alcohol product may comprise from 0.1 to 60 wt. % ethanol, e.g., from 5 to 55 wt. %, or from 10 to 50 wt. %. In terms of lower limits, the crude multi-carbon alcohol product may comprise at least 0.1 wt. % ethanol, e.g., at least 5 wt. %, or at least 10 wt. %. In terms of upper limits, the crude multi-carbon alcohol product may comprise at most 60 wt. % ethanol, at most 55 wt. % or at most 50 wt. %.

In one embodiment, the crude multi-carbon alcohol product may comprise from 1 to 30 wt. % water, e.g., from 8 to 25 wt. %, or from 10 to 20 wt. %. In terms of lower limits, the crude multi-carbon alcohol product may comprise at least 1 wt. % water, e.g., at least 8 wt. % or at least 10 wt. %. In terms of upper limits, the crude multi-carbon alcohol product may comprise at most 30 wt. % water, e.g., at most 25 wt. %, or at most 20 wt. %.

In one embodiment, the crude multi-carbon alcohol product comprises more ethanol than butanol, as measured and compared by weight. For example, the weight ratio of ethanol to butanol may be greater than 1:1, e.g., greater than 1.2:1, or greater than 1.4:1. The crude multi-carbon alcohol product may comprise more butanol than hexanol, as measured and compared by weight. For example, the weight ratio of butanol to hexanol may be greater than 2:1, e.g., greater than 4:1, or greater than 5:1.

In one embodiment the crude multi-carbon alcohol product may also comprise light organic compounds, e.g., light ends compounds, such as acetaldehyde, diethyl ether, butyraldehyde, and/or ethylene. For example, the crude multi-carbon alcohol product may comprise less than 15 wt. % of the light organic compounds, e.g., less than 10 wt. % or less than 6 wt. %. The crude multi-carbon alcohol product may comprise less than 8 wt. % acetaldehyde, e.g., less than 4 wt. %, or less than 1 wt. %; less than 10 wt. % diethyl ether, e.g., less than 5 wt. % or less than 2 wt. %, less than 8 wt. % butyraldehyde, less than 45 wt. % or less than 1 wt. %; less than 15 wt. % ethylene, e.g., less than 7 wt. %, or less than 2 wt. %.

In one embodiment, the crude multi-carbon alcohol product is substantially free of methanol, propanol, pentanol, and/or isotopes thereof. For example, the crude multi-carbon alcohol product comprises less than 1 wt. % of methanol, propanol, pentanol, and/or isotopes thereof. The crude multi-carbon alcohol product may also be substantially free of esters of butanol, ethanol, hexanol, methanol, pentanol, and/or octanol. For example the crude multi-carbon alcohol product comprise less than 5 wt. % of the esters of butanol, ethanol, hexanol, methanol, pentanol, and/or octanol. In one embodiment, the crude multi-carbon alcohol product is free of one of these components. In one embodiment, the crude multi-carbon alcohol product is substantially free of all of the components combined.

The crude multi-carbon alcohol product may be separated in a purification system comprising at least one, e.g., at least two or at least three, separation (distillation) zones. In one embodiment, the purification system comprises three distillation zones. The first distillation zone separates ethanol and light ends products from butanol, hexanol, and water. The second distillation zone separates water from butanol and hexanol. The third distillation zone separates butanol and hexanol. It has been surprisingly and unexpectedly found that the separation of ethanol and/or light ends from the crude product (in a first separation step) provides for effective separation of the crude multi-carbon alcohol product, as discussed above.

The inventive process comprises the step of separating at least a portion of the crude multi-carbon alcohol product in a first distillation zone to yield a first distillate and a first residue. Preferably, the crude multi-carbon alcohol product is fed to the first distillation zone in the liquid form or a mixture of liquid and vapor. The first distillate may comprise ethanol and light organic compounds, including but not limited to acetaldehyde, ethylene, butyraldehyde, and diethyl ether. In some cases, light end compounds are compounds in the reactor product having a boiling point is lower than the boiling point of ethanol at a given pressure (at a predetermined pressure).

In one embodiment, the first residue stream comprises butanol, water, and/or hexanol (if these components were present in the crude product). In one embodiment, the first residue comprises less than 0.5 wt. % ethanol, e.g., less than 0.1 wt. %, or less than 0.05 wt. %. The first residue may be substantially free of one or more light ends compounds selected from the group consisting of acetaldehyde, ethylene, butyraldehyde, and diethyl ether. For example, the first residue comprises less than 0.5 wt. % of the light ends compounds, either individually or as mixtures thereof.

In one embodiment, the first distillation zone comprises at least one column. Preferably, at least one of the at least one column, e.g., one column, operates at a top pressure above atmospheric pressure. For example, the column may operate at a top pressure above 10 psig, e.g., above 70 psig, or above 150 psig. As noted above, by operating the first column at an elevated pressure, less ethanol may be lost via the vent stream and/or the condenser may be operated at higher temperatures, e.g., it is not necessary to operate the condenser under cold conditions, e.g., a cooling brine is not necessary. In one embodiment, at least one of the at least one column, e.g., one column, may be operated at higher temperatures. For example the column may operate at a residue temperature greater than 90° C., e.g., greater than 140° C., or greater than 190° C.

Without being bound by theory, it is believed that the water forms a (heterogeneous) azeotrope with at least one of the multi-carbon alcohols, e.g., butanol and/or hexanol, in the first residue. These azeotropes can be utilized as discussed above, e.g., each can be separated, to yield the final product using minimal separation units.

It has now been discovered that pressure affects the behavior of such azeotropes, e.g., those present in the first residue. For example, when a column is operated under lower pressures, e.g., under a vacuum, the amount of water in the azeotrope increases. As another example, when a column is operated above atmospheric pressure, the amount of water in the azeotrope decreases.

In one embodiment, the process utilizes a second distillation zone to purify the first residue. Thus, the inventive process comprises the step of separating at least a portion of the first residue in the second distillation zone to form a second distillate and a second residue. The second distillate comprises, inter alia, water, and the second residue comprises butanol and optionally hexanol. The separation step removes water from the contents of the first residue, which include any azeotropes that may have formed.

In a preferred embodiment, the second distillation zone utilizes a configuration of at least two distillation columns to remove water from the multi-carbon alcohols. In one embodiment, at least a portion of the first residue is fed to the first of the two distillation columns of the second distillation zone to yield a second distillate and a second residue. In one embodiment, the first of the two distillation columns operates under low (top) pressure to beneficially increase the amount of water in the distillate. For example, the first of the two distillation columns operates at a top pressure lower than 150 psig, e.g., lower than 50 psig, or lower than 10 psig. As a result, the second residue has a lower water concentration. For example the second residue comprises less than 1 wt. % water, e.g., less than 0.5 wt. %, or less than 0.1 wt. %. The second residue comprises multiple-carbon alcohols, e.g., butanol and optionally hexanol. The second distillate and the second column of the two distillation columns is further discussed below. In one embodiment, the first of the at least two distillation columns operates at a top pressure lower than the top pressure of the second of the at least two distillation columns.

The second residue may be fed to a third distillation zone for separation. The third distillation zone may comprise one or more distillation column, e.g., a third column. The second residue may be fed to the third column to recover a third distillate comprising butanol and a third residue comprising hexanol. In one embodiment, the third distillate comprises from 95 to 99.99 wt. % butanol, e.g., from 97 to 99.99 wt %, from 97.5 to 99.9 wt. %, or from 98 wt. % to 99 wt. %; from 0.01 to 3 wt. % hexanol, e.g., from 0.1 to 2.5 wt. %, or from 1 to 2 wt. %; and from 0.01 to 1 wt. % water, e.g., from 0.1 to 0.8 wt. %, or from 0.3 to 0.6 wt. %. In one embodiment, because of the operations of the second distillation zone, the third distillate advantageously comprises more hexanol than water, as measured and compared by weight.

Returning to the second distillate, the second distillate from the first column of the two columns may comprise some butanol and water. In one embodiment, the second distillate comprises from 30 wt. % to 70 wt. % butanol and from 30 wt. % to 70 wt. % water. The second distillate may also comprise a small amount of ethanol and hexanol. For example, the second distillate may comprise at most 5 wt. % ethanol and at most 5 wt. % hexanol. The second distillate may be condensed in a condenser to form an organic phase and an aqueous phase. The organic phase comprises butanol and water and is returned to the first column as a reflux. Because of the operations of the first column of the second distillation zone, the amount of water in the organic phase is substantially less than the amount of water in the first residue. For example, the reflux stream comprises from 15 wt. % to 40 wt. % water, e.g., from 25 wt. % to 35 wt. %, or from 28 wt. % to 32 wt. %.

The aqueous phase comprises mostly water, of course. For example, the water phase comprises greater than 85 wt. % water, e.g., greater than 92 wt. %, or greater than 95 wt. %. The water phase may also comprise some butanol, e.g., an amount less than 10 wt. %, less than 8 wt. %, or less than 5 wt. %. The water phase is fed to the second of the two distillation columns in the second distillation zone to form a residue comprising water and a distillate. This column may be operated at a pressure higher than atmospheric, to reduce the amount of water in the azeotrope and therefore reduce the amount of energy required to recover the butanol dissolved in the aqueous phase fed to the column. For example the distillation column operates at a top pressure greater than 2 psig, e.g., greater than 20 psig, or greater than 60 psig. In one embodiment, the first column of the two columns in the second distillation zone operates at a top pressure lower than that of the second column of the two columns. In these cases, the water content of the resultant distillates and residues, beneficially, can be adjusted. The residue of the second column comprises greater than 99 wt. % water, e.g., greater than 99.5 wt. % water, or greater than 99.9 wt. % water. In one embodiment, the distillate comprises water, butanol and ethanol and is returned to the condenser. In one embodiment, the distillate comprises from 30 wt. % to 70 wt. % butanol and from 30 wt. % to 70 wt. % water.

Returning to the first distillation zone, in one embodiment, ethanol may be recovered from the first distillate and optionally returned to the reactor (to generate additional multi-carbon alcohols). In one embodiment, the first distillate comprises greater than 70 wt. % ethanol, e.g., greater than 75 wt. %, or greater than 80 wt. %. The process may further comprise the steps of condensing at least a portion of the first distillate and removing a vent stream comprising the one or more light ends compounds from the condensed portion. The condensed first distillate may comprise greater than 70 wt. % ethanol, e.g., greater than 75 wt. % or greater than 85 wt. %. The condensed first distillate may further comprise from 0.001 to 2 wt. % butanol, e.g., from 0.01 to 2 wt. % butanol, or from 0.1 to 2 wt. %. In one embodiment, a compressor may be used in conjunction with the distillation column. It has now been found that when the distillation column is operated at atmospheric pressure, a partial compressor may surprisingly be used to separate light ends products from ethanol. In another embodiment, the distillation column may be operated at high pressure. For example, the distillation column may be operated at a top pressure above 10 psig, e.g., above 70 psig, or above 150 psig. The distillation column may be operated at a temperature greater 90° C., e.g., greater than 140° C., or greater than 190° C. In one embodiment, the condensed first distillate, which comprises ethanol, may be fed to the reactor. In another embodiment, multiple columns may be used to separate the components of the first distillate.

In a preferred embodiment, no extractive agents are utilized in the first, second, and/or third distillation zone. As a result, equipment and/or process cost are beneficially reduced.

Catalyst Composition

The catalyst used in the reaction of the present invention may vary widely. Examples of conventional catalysts include hydroxyapatite and phosphate derivatives.

In addition to these conventional catalysts, it has now been discovered that certain catalysts effectively oxidize ethanol to form an intermediate aldehyde, which forms crotonaldehyde, and reduces crotonaldehyde to butanol. Without being bound by theory, it is believed that these catalysts serve as a base to oxidize ethanol and promote aldol condensation, and also as a hydrogenating site in the formation of butanol from crotonaldehyde. The inventors have found that a catalyst system of hydrotalcite (HT) coated with one or more metals beneficially results in the improvement of ethanol conversion, and/or butanol selectivity of butanol. The metal coated HT comprises one or more metals (M) selected from the group consisting of magnesium, aluminum, gallium, germanium, tin, lead, copper, and other transition metals.

In another embodiment, the inventors have found that a catalyst system of at least one alkali metal and a metal coated on a support beneficially results in the improvement of ethanol conversion, and/or butanol selectivity. Preferably, the metal is selected from the group consisting of palladium, platinum, copper, nickel, and cobalt. In another embodiment, the inventors also found that a catalyst system of one or more metals coated on a support beneficially results in the improvement of ethanol conversion, and/or butanol selectivity. The metals are selected from the group consisting of cobalt, nickel, palladium, platinum, iron, zinc, tin and copper. The support is selected from the group consisting of $Al_2O_3$, $ZrO_2$, MgO, $TiO_2$, zeolite, ZnO, and mixtures thereof. The metals discussed herein may be present as a metallic metal or a metal oxide.

"Hydrotalcite" (HT) as used in the present application generally refers to a commercially available hydrotalcite such as magnesium aluminum hydroxycarbonate, having a chemical formula: $Mg_6Al_2CO_3(OH)_{16} \cdot 4H_2O$. Synthetic magnesium aluminum hydroxycarbonate may be obtained from Sigma-Aldrich. Of course, synthesized or natural hydrotalcite having a similar chemical formula may also be used to make the catalyst composition.

Alumina supports may include gamma-alumina ($\gamma$-$Al_2O_3$), etu-alumina ($\eta$-$Al_2O_3$), kappa alumina ($\kappa$-$Al_2O_3$), theta-alumina ($\theta$-$Al_2O_3$), or other alumina phase which is stable at temperatures use for catalyst calcination and conversion of alcohols, such as ethanol, to other alcohols, such as butanol.

Zeolite as used in the present application generally refers to microporous, aluminosilicate minerals. Examples of suitable zeolites include, but not limited to, silicoaluminophosphate (SAPO-34), clinoptilolite, ZSM-5, X-zeolite, Y-zeolite.

In one embodiment, the catalyst comprises a metal in an amount from 0.01 wt. % to 20 wt. %, e.g., from 0.05 wt. % to 18 wt. %, or from 0.1 wt. % to 16 wt. %. The amount of support may vary depending on the metal loadings and generally comprises the balance of the catalyst. In one embodiment, the catalyst comprises the support in an amount from 80 wt. % to 99.99 wt. %, e.g., from 82 wt. % to 99.95 wt. %, or from 84 wt. % to 99.9 wt. %.

"Coat," "coated," or "coating" as used in the present application generally refers to one or more metals distributed on the surface of hydrotalcite. This distribution on the surface forms a metal-coated hydrotalcite complex.

Water is a byproduct when converting ethanol to butanol. Since water is more polar than ethanol, it is believed that water might compete with ethanol on the polar surface of the catalyst. The inventors have found that the surface polarity of the catalysts may be modified by introducing an organic metal precursor to the surface of the support to minimize the water/ethanol competition. The organic metal precursor may include pyridine, ammonium hydroxide tetramethylammonium hydroxide, tetrabutylammonium hydroxide, methyl amine, imidazole, and other suitable support modifiers. The organic metal precursors may be support modifiers that may adjust the chemical or physical properties of the support material such as the acidity or basicity of the support material. In one embodiment, the support material is hydrotalcite. The amount and residence time of ethanol on the surface of the catalyst may be increased, thereby promoting the carbon-carbon capillary condensation.

The catalyst may further comprise other additives, examples of which may include: molding assistants for enhancing moldability; reinforcements for enhancing the strength of the catalyst; pore-forming or pore modification agents for formation of appropriate pores in the catalyst, and binders. Examples of these other additives include stearic acid, graphite, starch, cellulose, silica, alumina, glass fibers, silicon carbide, and silicon nitride. Preferably, these additives do not have detrimental effects on the catalytic performances, e.g., conversion and/or activity. These various additives may be added in such an amount that the physical strength of the catalyst does not readily deteriorate to such an extent that it becomes impossible to use the catalyst practically as an industrial catalyst.

In some embodiments the catalyst composition comprises a pore modification agent, such as oxalic acid. A preferred type of pore modification agent is thermally stable and has a substantial vapor pressure at a temperature below 300° C., e.g., below 250° C. In one embodiment, the pore modification agent has a vapor pressure of at least 0.1 kPa, e.g., at least 0.5 kPa, at a temperature between 150° C. and 250° C., e.g., between 150° C. and 200° C.

The pore modification agent has a relatively high melting point, e.g., greater than 60° C., e.g., greater than 75° C., to prevent melting during the compression of the catalyst into a slug, tablet, or pellet. Preferably, the pore modification agent comprises a relatively pure material rather than a mixture. As such, lower melting components will not liquefy under compression during formation of slugs or tablets. For example, where the pore modification agent is a fatty acid, lower melting components of the fatty acid mixtures may be removed as liquids by pressing. If this phenomenon occurs during slug or tablet compression, the flow of liquid may disturb the pore structure and produce an undesirable distribution of pore volume as a function of pore diameter on the catalyst composition. In other embodiments, the pore modification agents have a significant vapor pressure at temperatures below their melting points, so that they can be removed by sublimation into a carrier gas.

Production of Multi-carbon Alcohols

In one embodiment, the crude multi-carbon alcohol product is produced via an ethanol condensation reaction. In one embodiment, the crude multi-carbon alcohol product is the product of a vapor phase reaction.

In some embodiments, the condensation reaction may achieve favorable conversion of ethanol and favorable selectivity and productivity to butanol. For purposes of the present invention, the term "conversion" refers to the amount of ethanol in the feed that is converted to a compound other than ethanol. Conversion is expressed as a percentage based on ethanol in the feed. The conversion of ethanol may be at least 28%, e.g., at least 30%, at least 40%, or at least 60%.

The feed stream comprises ethanol. Preferably, the (gaseous) feed stream comprises more than 5 vol. % ethanol, e.g., more than 10 vol. % or more than 20 vol. %. The feedstream may also comprise other molecules such as pyridine, $NH_3$, and alkyl amine. Inert gases may be in the gaseous stream and thus may include nitrogen, helium, argon, and methane. Preferably, no hydrogen is introduced with the gaseous stream, and thus the gaseous stream is substantially free of hydrogen. Without being bound by theory the hydrogen needed for the intermediate reactions may be produced in situ.

Selectivity, as it refers to the formation of butanol, is expressed as the ratio of the amount of carbon in the desired product(s) and the amount of carbon in the total products. Preferably, the selectivity to butanol is at least 30%, e.g., at least 40%, or at least 60%. In some embodiments, the catalyst selectivity to $C_{4+}$ alcohols, e.g., n-butanol, isobutanol, 2-butanol, tert-butanol, 1-hexanol, 2-ethylbutanol, or 2-ethylhexanol, is at least 30%, e.g., at least 50%, at least 60%, or at least 80%.

Preferred embodiments of the inventive process demonstrate a low selectivity to undesirable products, such as DEE and ethylene. The selectivity to these undesirable products preferably is less than 20%, e.g., less than 5% or less than 1%. More preferably, these undesirable products are not detectable.

The ethanol may be fed to the reactor as a liquid stream or a vapor stream. Preferably, the ethanol is fed as a vapor stream. In one embodiment, the ethanol stream is substantially free of hydrogen, e.g., less than 1 wt. % hydrogen, less than 0.1 wt. %, or less than 0.01 wt. %.

The reactor may be any suitable reactor or combination of reactors. Preferably, the reactor comprises a fixed bed reactor or a series of fixed bed reactors. In one embodiment, the reactor is a gas flow catalytic reactor or a series of gas flow catalytic reactors. Of course, other reactors such as a continuous stirred tank reactor or a fluidized bed reactor, may be employed.

The condensation reaction may be conducted at a temperature of at least 250° C., e.g., at least 300° C., or at least 350° C. In terms of ranges, the reaction temperature may range from 200° C. to 500° C., e.g., from 250° C. to 400° C., or from 250° C. to 350° C. Residence time in the reactor may range from 0.01 to 100 hours, e.g., from 1 to 80 hours, or from 5 to 80 hours. Reaction pressure is not particularly limited, and the reaction is typically performed near atmospheric pressure. In one embodiment, the reaction may be conducted at a pressure ranging from 0.1 kPa to 9,000 kPa, e.g., from 20 kPa to 5,000 kPa, or from 90 to 3500 kPa. The ethanol conversion may vary depending upon the reaction temperature and/or pressure.

In one embodiment, the reaction is conducted at a gas hourly space velocity ("GHSV") greater than 600 $hr^{-1}$, e.g., greater than 1000 $hr^{-1}$ or greater than 2000 $hr^{-1}$. The GHSV may range from 600 $hr^{-1}$ to 10000 $hr^{-1}$, e.g., from 1000 $hr^{-1}$ to 8000 $hr^{-1}$ or from 1500 $hr^{-1}$ to 7500 $hr^{-1}$.

An inert or reactive gas may be supplied to the reactant stream. Examples of inert gases include, but are not limited to, nitrogen, helium, argon, and methane. Examples of reactive gases or vapors include, but are not limited to, oxygen, carbon oxides, sulfur oxides, and alkyl halides. When reactive gases such as oxygen are added to the reactor, these gases, in some embodiments, may be added in stages throughout the catalyst bed at desired levels as well as feeding with the other feed components at the beginning of the reactors. The addition of these additional components may improve reaction efficiencies.

In one embodiment, the unreacted components such as the ethanol as well as the inert or reactive gases that remain are recycled to the reactor after sufficient separation from the desired product.

Separation

As discussed above, the reaction mixture of multi-carbon alcohols is separated in one or more distillation zones. FIG. 1 is a schematic diagram of a multi-carbon alcohol reaction and separation system in accordance with one embodiment of the present invention. System 100 comprises reaction zone 102, first separation zone 104, second separation zone 106, and third separation zone 108. Reaction zone 102 comprises reactor 110, ethanol feed, 112, and vaporizer 114.

Ethanol is fed to vaporizer 114 via ethanol feed 112. Vaporizer 114 creates a vapor feed stream, which exits vaporizer 114 via line 116 and is directed to reactor 110. The temperature of the vapor feed stream in line 116 is preferably from 150° C. to 600° C., e.g., from 250° C. to 500° C. or from 340° C. to 425° C. Alternatively, a vaporizer may not be employed and ethanol may be fed directly to reactor 110.

Any feed that is not vaporized may be removed from vaporizer 114 and may be recycled or discarded. In addition, although line 116 is shown as being directed to the upper half of reactor 110, line 116 may be directed to the middle or bottom of reactor 110.

Reactor 110 contains the catalyst that is used in the reaction to form crude multi-carbon alcohol product, which is withdrawn, preferably continuously, from reactor 110 via line 118. Although FIG. 1 shows the crude multi-carbon alcohol product being withdrawn from the bottom of reactor 110, the crude multi-carbon alcohol product may be withdrawn from any portion of reactor 110. Exemplary composition ranges for the crude multi-carbon alcohol product are shown in Table 1.

TABLE 1

| CRUDE MULTI-CARBON ALCOHOL PRODUCT COMPOSITIONS | | | |
|---|---|---|---|
| Component | Conc. (wt %) | Conc. (wt %) | Conc. (wt %) |
| Ethanol | 0.1 to 60 | 5 to 50 | 10 to 50 |
| Butanol | 15 to 80 | 15 to 70 | 20 to 75 |
| Water | 1 to 3 | 1 to 70 | 5 to 50 |
| Hexanol | 0.1 to 30 | 2 to 15 | 5 to 15 |
| Diethyl ether | 0.01 to 5 | 0.1 to 4 | 0.1 to 3 |
| Ethylene | 0.01 to 5 | 0.1 to 4 | 0.1 to 2 |
| Acetaldehyde | 0.1 to 3 | 0.1 to 2 | 0.5 to 1 |
| Butyraldehyde | 0.01 to 2 | 0.1 to 1.5 | 0.1 to 1 |

Figure 2:
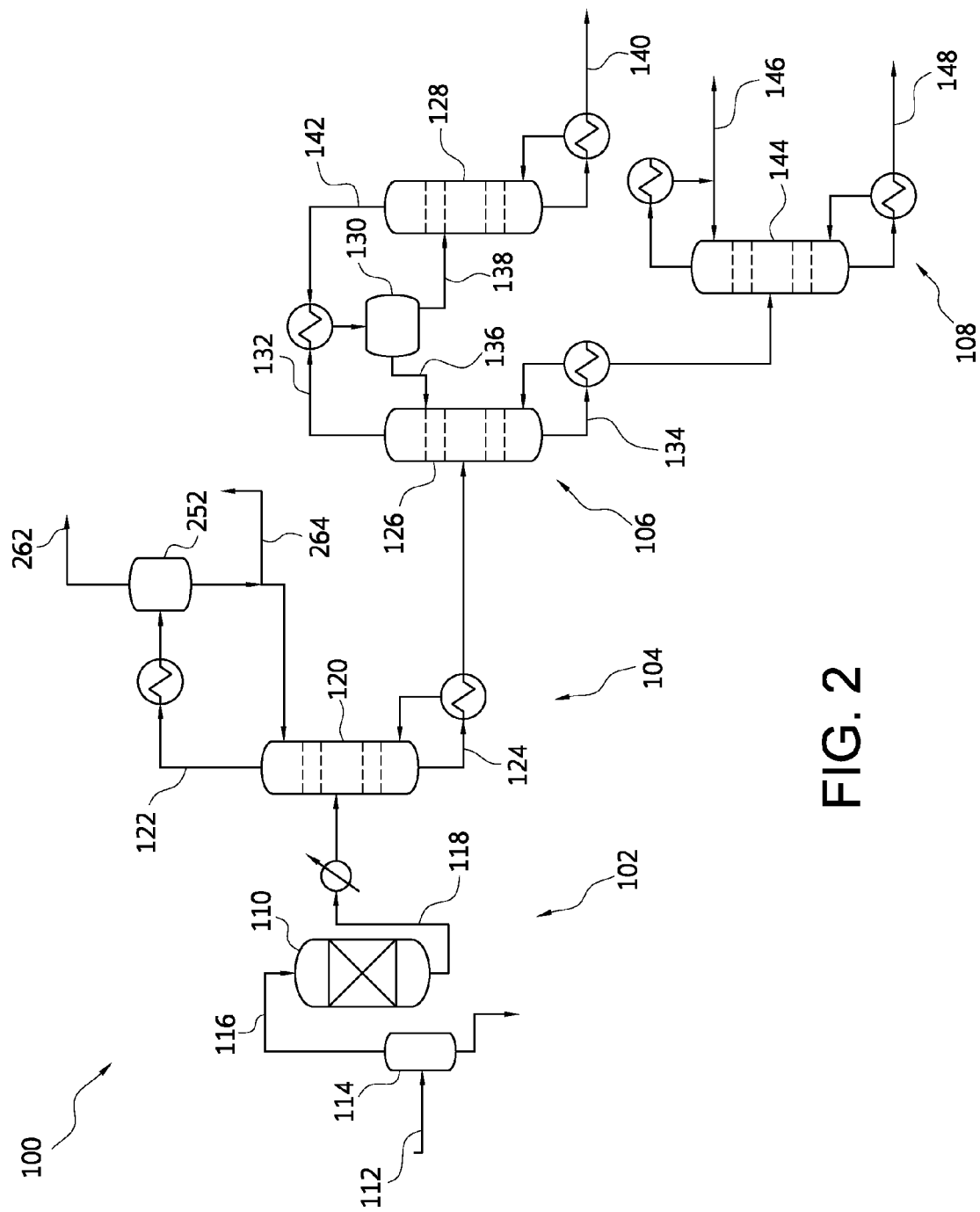
FIG. 2 is a schematic diagram of a multi-carbon alcohols separation system in accordance with one embodiment of the present invention.
Figure 3:
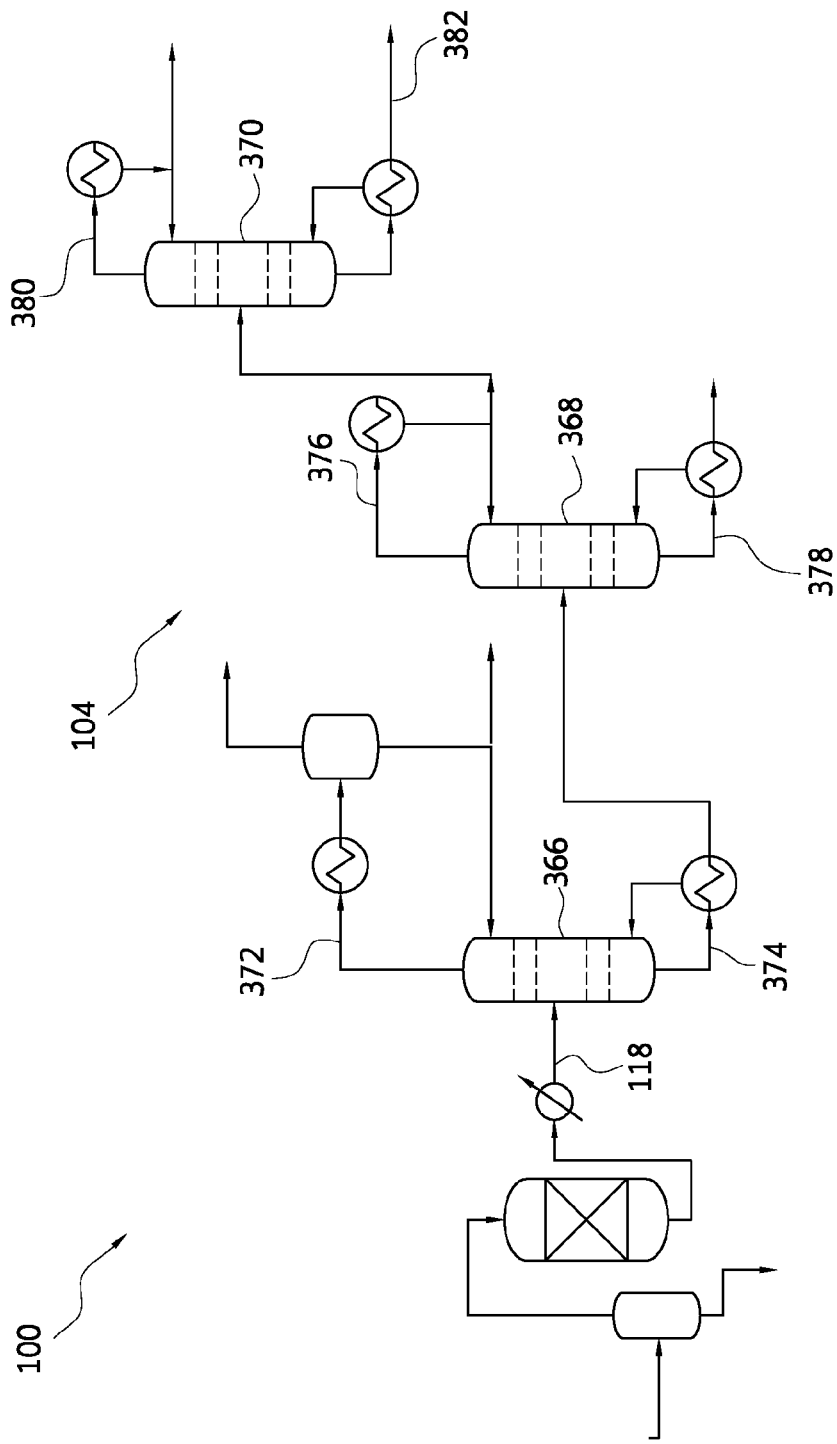
FIG. 3 is a schematic diagram of a portion of a multi-carbon alcohols separation system in accordance with one embodiment of the present invention.

The crude multi-carbon alcohol product in line 118 is fed to first separation zone 104. First separation zone 104 may comprise one or more distillation columns and/or other components such as flashers or compressors. In one example, the first separation zone comprises one column, two flashers, and one compressor, as shown in FIG. 1. In another example, the first separation zone comprises one column and one flasher, as shown in FIG. 2. In another embodiment, the first separation zone comprises three columns and one flasher, as shown in FIG. 3.

First separation zone 104 comprises first column 120, which separates at least a portion of the crude multi-carbon alcohol product in line 118 into an overhead stream, e.g., a first distillate, which exits first column 120 via line 122 and a residue stream, which exits via line 124. For convenience, the distillate and residue of the first column may also be referred to as the "first distillate" or "first residue." The distillates or residues of the other columns may also be referred to with similar numeric modifiers (second, third, etc.) in order to distinguish them from one another, but such modifiers should not be construed as requiring any particular separation order.

The first distillate in line 122 is refluxed and the first residue in line 124 is boiled up as shown. The first residue comprises less than 0.5 wt. % ethanol. The first residue is substantially free of one or more light ends compounds selected from the group consisting of acetaldehyde, ethylene, butyraldehyde and diethyl ether. Exemplary compositional ranges for first distillate in line 122 and first residue in line 124 are shown in Table 2. Components other than those listed in Table 2 may also be present in the streams. Examples include carbon dioxide, carbon monoxide, oxygen, nitrogen, and hydrogen.

TABLE 2

FIRST COLUMN COMPOSITION

|  | Conc. (wt %) | Conc. (wt %) | Conc. (wt %) |
|---|---|---|---|
| First Distillate |  |  |  |
| Ethanol | >5 | 5 to 99 | 55 to 90 |
| Butanol | <1 | <0.1 | <0.05 |
| Water | <25 | 0.1 to 10 | 0.5 to 7 |
| Hexanol | <25 | 0.1 to 15 | 1 to 10 |
| Diethyl ether | >0.1 | 0.1 to 5 | 0.1 to 3 |
| Ethylene | >0.01 | 0.01 to 1 | 0.1 to 5 |
| Acetaldehyde | >0.1 | 0.1 to 5 | 1 to 3 |
| Butyraldehyde | >0.1 | 0.1 to 5 | 1 to 3 |
| First Residue |  |  |  |
| Ethanol | <0.5 | <0.1 | <0.05 |
| Butanol | >30 | >40 | >50 |
| Water | <50 | 5 to 40 | 10 to 30 |
| Hexanol | >1 | >8 | >10 |
| DEE | <0.5 | <0.1 | <0.05 |
| Ethylene | <0.5 | <0.1 | <0.05 |
| Acetaldehyde | <0.5 | <0.1 | <0.05 |
| Butyraldehyde | <0.5 | <0.1 | <0.05 |

At least a portion of first residue in line 124 is directed to second distillation zone 106. Second distillation zone 106 may be referred to as a dehydration zone and comprises two columns 126, 128 and a phase separator 130. Column 126 separates the at least a portion of the first residue in line 124 into a second distillate in line 132 and a second residue (dehydrated alcohol stream) in line 134. The second residue in line 134 comprises one or more alcohols, e.g., multi-carbon alcohols, such as butanol and/or hexanol, and less than 1 wt. % water.

The second distillate in line 132 is condensed and fed to phase separator 130. Phase separator 130 yields an organic phase in line 136 and an aqueous phase in line 138. In one embodiment, column 126 is operated at a lower pressure, as discussed herein. As previously noted, without being bound by theory, it is believed that at low pressure, the amount of water is increased in the azeotrope. Thus, more water is removed in second distillate in line 132. As a result, second residue in line 134 comprises less than 1 wt. % water, e.g., less than 0.5 wt. %, or less than 0.1 wt. %. The second residue in line 134 comprises butanol and hexanol. Although the FIGS. show one phase separator, other embodiment contemplate a configuration in which each column has a phase separator.

Exemplary compositional ranges for second distillate in line 132 and second residue in line 134 are shown in Table 3. Components other than those listed in Table 3 may also be present in the streams.

TABLE 3

SECOND COLUMN COMPOSITION

|  | Conc. (wt %) | Conc. (wt %) | Conc. (wt %) |
|---|---|---|---|
| Second Distillate |  |  |  |
| Ethanol | <5 | 0.1 to 5 | 1 to 3 |
| Butanol | 30 to 70 | 35 to 60 | 35 to 55 |
| Water | 30 to 70 | 35 to 60 | 35 to 55 |
| Hexanol | <5 | 0.1 to 5 | 1 to 3 |
| Second Residue |  |  |  |
| Ethanol | <0.5 | <0.1 | <0.05 |
| Butanol | >50 | 50 to 95 | 60 to 85 |
| Water | <2 | <1 | 0.01 to 0.1 |
| Hexanol | >0.01 | >1 | >5 |

Phase separator 130 separates the second distillate in line 132 into an organic phase 136 and an aqueous phase 138. The organic phase comprises butanol and water. Organic phase 136 may be refluxed to column 126. The second residue in line 134 may be boiled up as shown. The aqueous phase in line 138 may be further processed (downstream). Thus, phase separator 130 reduces the amount of water that is returned to column 126. For example, the reflux stream comprises from 15 wt. % to 40 wt. % water, e.g., from 25 wt. % to 35 wt. %, or from 28 wt. % to 32 wt. %. Exemplary composition ranges for the aqueous and organic phases of phase separator 130 are shown in Table 4. Components other than those listed in Table 4 may also be present in the two phases.

TABLE 4

PHASE SEPARATOR COMPOSITION

|  | Conc. (wt. %) | Conc. (wt. %) | Conc. (wt. %) |
|---|---|---|---|
| Aqueous |  |  |  |
| Ethanol | <5 | 0.1 to 4 | 0.1 to 1 |
| Butanol | <20 | 1 to 15 | 5 to 10 |
| Water | >70 | 75 to 95 | 85 to 95 |
| Hexanol | <1 | 0.001 to 0.5 | 0.01 to 0.5 |
| Organic |  |  |  |
| Ethanol | <10 | 0.1 to 8 | 1 to 5 |
| Butanol | 20 to 90 | 40 to 80 | 50 to 70 |
| Water | 10 to 50 | 15 to 40 | 20 to 35 |
| Hexanol | <10 | 0.1 to 8 | 1 to 5 |

The aqueous phase 138 comprises mostly water and is fed to column 128 to yield a purified water stream in line 140 and a distillate in line 142. The distillate in line 142 comprises most of the alcohols in the aqueous phase 138 and is condensed and returned to phase separator 130. For example, the distillate in line 142 comprises greater than 5 wt. % butanol, e.g., greater than 15 wt. %, or greater than 30 wt. %.

In one embodiment, the temperature of the purified water stream in line 140 exiting column 128 ranges from 30° C. to 200° C., e.g., from 60° C. to 140° C. or from 80° C. to 120° C. The temperature of the distillate exiting column 128 preferably ranges from 30° C. to 200° C., e.g., from 60° C. to 140° C. or from 80° C. to 120° C. The pressure at which column 128 is operated may range from 0.01 to 30 bar, e.g., from 0.1 to 10 bar or from 0.5 to 5 bar.

Exemplary composition ranges for distillate in line 142 and residue in line 140 are shown in Table 5. Components other than those listed in Table 5 may also be present in the distillate and the residue.

TABLE 5

COLUMN COMPOSITION

|  | Conc. (wt. %) | Conc. (wt. %) | Conc. (wt. %) |
|---|---|---|---|
| Distillate |  |  |  |
| Ethanol | <5 | 0.1 to 5 | 1 to 3 |
| Butanol | 30 to 70 | 35 to 60 | 35 to 55 |
| Water | 30 to 70 | 35 to 60 | 35 to 55 |
| Hexanol | <5 | 0.1 to 5 | 1 to 3 |
| Residue |  |  |  |
| Ethanol | <5 | <1 | <0.1 |
| Butanol | <1 | <0.1 | <0.01 |
| Water | >90 | 95 to 99.99 | 99.5 to 99.99 |
| Hexanol | <5 | <1 | <0.1 |

Returning to second column 126, at least a portion of the dehydrated alcohol residue in line 134 is conveyed to third distillation zone 108 to recover the alcohol products. Third distillation zone 108 comprises at least one column, e.g., third column 144. As shown in FIG. 1, at least a portion of second residue in line 134 is fed to third column 144 to yield a butanol stream in line 146 and a hexanol stream in line 148. Depending on the composition of butanol versus hexanol in the second residue, line 134 may be fed in the middle of third column 144 as shown. In another embodiment, line 134 may be fed to the top half of third column 144, e.g., top third, or top fourth of the column.

In one embodiment, the temperature of the residue exiting third column 144 ranges from 60° C. to 350° C., e.g., from 100° C. to 300° C. or from 125° C. to 250° C. The temperature of the distillate exiting third column 144 preferably ranges from 50° C. to 200° C., e.g., from 80° C. to 160° C. or from 100° C. to 130° C. The top pressure at which the column(s) are operated may range from 1 kPa to 3000 kPa, e.g., from 50 kPa to 1500 kPa or from 80 kPa to 1000 kPa.

Exemplary composition ranges for the distillate and residue of third column 144 are shown in Table 6. Components other than those listed in Table 6 may also be present in the residue or distillate.

TABLE 6

THIRD COLUMN COMPOSITION

|  | Conc. (wt. %) | Conc. (wt. %) | Conc. (wt. %) |
|---|---|---|---|
| Distillate |  |  |  |
| Ethanol | <1 | <0.01 | <0.01 |
| Butanol | 95 to 99.99 | 97 to 99.99 | 99 to 99.99 |
| Water | <3 | <0.5 | <0.1 |
| Hexanol | <3 | <0.5 | <0.1 |
| Residue |  |  |  |
| Ethanol | <1 | <0.01 | <0.01 |
| Butanol | <3 | <0.5 | <0.1 |
| Water | <1 | <0.01 | <0.01 |
| Hexanol | >95 | 95 to 99.99 | 99 to 99.99 |

Returning to first distillation zone 104, first distillation column 120 separates crude multi-carbon alcohol product 118 into the first distillate in line 122 and the first residue in line 124. As stated above, the first distillate comprises ethanol and light ends compounds. In one embodiment, the first distillate may be fed to ethanol recovery system 150 to yield an ethanol stream, which may be recycled to the reactor to generate more multi-carbon alcohols.

In one embodiment, ethanol recovery system 150 comprises one or more flashers and compressors. As shown in FIG. 1, ethanol recovery system 150 comprises flashers 152, 154 and compressor 156. First distillate in line 122 is cooled and then fed to flasher 152. Flasher 152 yields a first vent stream 158 and a reflux distillate 160. First vent stream 158 comprises ethanol, and light ends compounds, including acetaldehyde, diethyl ether, butyraldehyde, and ethylene. Specifically, first vent stream 158 comprises greater than 20 wt. % ethanol, greater than 40 wt. % and greater than 65 wt. %. In order to recover additional ethanol, first vent stream 158 is fed to compressor 156 and then to a second flasher 154. In preferred embodiments, the stream exiting compressor 156 may be fed to a heat exchanger (not shown) to cool the stream prior to being fed to flasher 154. Second flasher 154 flashes the compressed stream into a second vent stream 162 and ethanol recycle stream 164.

In one embodiment, at least a portion of reflux distillate 160 is returned to first column 120. At least a portion of reflux distillate 160 may be combined with ethanol recycle stream 164. Ethanol recycle stream 164 comprises greater than 95% of the ethanol in crude multi-carbon alcohol product in line 118, e.g., greater than 99%, or greater than 99.5%. Ethanol recycle stream 164 may also comprise water, diethyl ether, acetaldehyde, butyraldehyde, and ethylene.

Second vent stream 162 comprises mostly light ends compounds. For example, second vent stream 162 comprises greater than 70 wt. % light ends compounds, e.g., greater than 80 wt. %, or greater than 90 wt. %. Second vent stream 162 may be removed from the system.

In another embodiment, as shown in FIG. 2, the pressure of the first column may be modified so as to reduce the need for a compressor for the ethanol recovery system. For example, it has been found that by increasing the pressure of first column to greater than atmospheric pressure, greater than 90% of the ethanol in the crude multi-carbon alcohol product may be recovered, e.g, greater than 92%, or greater than 94%. By modifying the pressure of the first column, the capital cost of an additional compressor, condenser and flasher, beneficially, may be reduced or eliminated entirely. As shown in FIG. 2, first distillate 122 is condensed and fed to flasher 252 to yield a vent stream 262 and an ethanol recycled stream 264. In one embodiment, the ethanol recycled stream 264 comprises mostly ethanol. For example, ethanol recycled stream 264 comprises great than 50 wt. % ethanol, e.g., greater than 70 wt. % and greater than 80 wt. %. Vent stream 262 may be removed from the system.

In some embodiments, first distillation zone 104 may comprise multiple distillation columns. In FIG. 3, first distillation zone 104 comprises columns, 366, 368, 370. In the embodiment of FIG. 3, column 366 is operated such that light ends compounds are separated into the distillate in line 372 and water and alcohols are separated into the residue in line 374. As shown, crude multi-carbon alcohol product 118 is fed to distillation column 366 to form a distillate comprising light end compounds in line 372 and a residue comprising water and alcohols, including ethanol, butanol, and hexanol in line 374. A portion of distillate in line 372 may be condensed and refluxed and another portion may be vented from the system. The distillate in line 372 comprises less than 5 wt. % of combined butanol and hexanol, and may comprise up to 20 wt. % ethanol.

The residue in line 374 comprises ethanol, butanol, hexanol, and water. The residue in line 374 is fed to second distillation column 368 to remove ethanol from the residue in line 374 to yield an ethanol enriched stream in line 376 and residue in line 378. The residue in line 378 comprises butanol, hexanol and water and may be fed to second distillation zone 106 (discussed herein).

Ethanol enriched stream 376 comprises ethanol, water and small amount of light ends compounds, such as butyraldehyde. For example, ethanol enriched stream 376 comprises greater than 60 wt. % ethanol, greater than 75 wt. %, or greater than 90 wt. %; less than 30 wt. % light ends compounds, e.g., less than 15 wt. %, or less than 10 wt. %.

Light ends compounds may cause undesirable side-products if returned to the reactor (with the accompanying ethanol). As shown in FIG. 3, ethanol enriched stream 376 is fed to a distillation column 370 to remove the light ends compounds. Distillation column 370 yields a light ends compound stream in line 380 and a purified ethanol stream in line 382. In one embodiment, light ends compound stream 380 comprises at least 20 wt. % light ends compounds, e.g., at least 40 wt. %, or at least 55 wt. %. This stream may be utilized for heat value or may be flared. In one embodiment, purified ethanol stream 382 comprises less than 0.5 wt. % light ends compounds, e.g., less than 0.1 wt. %, or less than 0.01 wt. %. In some embodiment, purified ethanol stream 382 may comprise water in an amount of less than 20 wt. %, e.g., less than 15 wt. %, or less than 10 wt. %. Purified ethanol stream 382 may be returned to the reactor.

EXAMPLES

Example 1

A simulation of a process in accordance with FIG. 1 was conducted using ASPEN™ software. The compositions of the various process streams are shown in Table 7.

TABLE 7

SIMULATED COMPOSITIONAL DATA FOR PROCESS STREAMS

| Comp. | Feed | First Residue | First Distillate | Vent to Compressor | Vent to Flare | Recycle stream | Second Distillate | Second Residue | Third Distillate | Third Residue | Fourth Distillate | Fourth Residue |
|---|---|---|---|---|---|---|---|---|---|---|---|---|
| Ethanol | 41.33 | 0.02 | 86.48 | 65.20 | 5.31 | 83.97 | 1.84 | 0.00 | 4.86 | 0.07 | 0.00 | 0.00 |
| Butanol | 30.31 | 61.90 | 0.013 | 0.01 | 0.00 | 0.01 | 48.45 | 82.28 | 47.72 | 0.00 | 99.85 | 0.05 |
| Water | 16.07 | 24.78 | 8.31 | 6.06 | 0.44 | 8.01 | 48.10 | 0.05 | 47.33 | 99.9 | 0.06 | 0.00 |
| Hexanol | 6.51 | 13.30 | 0.00 | 0.00 | 0.00 | 0.00 | 1.61 | 17.67 | 0.09 | 0.03 | 0.09 | 99.95 |
| DEE | 2.14 | 0.00 | 2.15 | 10.03 | 13.49 | 3.82 | 0.00 | 0.00 | 0.00 | 0.00 | 0.00 | 0.00 |
| Ethylene | 1.90 | 0.00 | 0.26 | 13.66 | 75.25 | 0.89 | 0.00 | 0.00 | 0.00 | 0.00 | 0.00 | 0.00 |
| Acetaldehyde | 1.01 | 0.00 | 1.53 | 3.24 | 1.94 | 1.97 | 0.00 | 0.00 | 0.00 | 0.00 | 0.00 | 0.00 |
| Butyraldehyde | 0.65 | 0.00 | 1.26 | 1.31 | 0.27 | 1.31 | 0.00 | 0.00 | 0.00 | 0.00 | 0.00 | 0.00 |

Example 2

A simulation of a process in accordance with FIG. 2 was conducted using ASPEN™ software. The compositions of the various process streams are shown in Table 8.

TABLE 8

SIMULATED COMPOSITIONAL DATA FOR PROCESS STREAMS

| Composition | Feed | First Residue | First Distillate | Vent | Second Distillate | Second Residue | Third Distillate | Third Residue | Fourth Distillate | Fourth Residue |
|---|---|---|---|---|---|---|---|---|---|---|
| Ethanol | 41.33 | 0.02 | 82.90 | 61.72 | 1.80 | 0.00 | 4.63 | 0.06 | 0.00 | 0.00 |
| Butanol | 30.31 | 61.53 | 0.01 | 0.01 | 48.65 | 82.28 | 47.72 | 0.00 | 99.85 | 0.05 |
| Water | 16.07 | 25.22 | 7.33 | 5.42 | 47.72 | 0.05 | 47.55 | 99.90 | 0.06 | 0.00 |
| Hexanol | 6.51 | 13.23 | 0.00 | 0.00 | 1.82 | 17.67 | 0.10 | 0.03 | 0.09 | 99.95 |
| DEE | 2.14 | 0.00 | 4.13 | 5.39 | 0.00 | 0.00 | 0.00 | 0.00 | 0.00 | 0.00 |
| Ethylene | 1.90 | 0.00 | 2.34 | 22.77 | 0.00 | 0.00 | 0.00 | 0.00 | 0.00 | 0.00 |
| Acetaldehyde | 1.01 | 0.00 | 1.99 | 1.86 | 0.00 | 0.00 | 0.00 | 0.00 | 0.00 | 0.00 |
| Butyraldehyde | 0.65 | 0.00 | 1.30 | 1.03 | 0.00 | 0.00 | 0.00 | 0.00 | 0.00 | 0.00 |

Example 3

A simulation of a process in accordance with FIG. 3, and also including other elements, was conducted using ASPEN™ software. The compositions of the various process streams are shown in Table 9.

TABLE 9

SIMULATED COMPOSITIONAL DATA FOR PROCESS STREAMS

| Comp. | Feed | First Distillate | Vent | First Residue | Second Distillate | Second Residue | Third Distillate | Third Residue | Fourth Distillate | Fourth Residue | Fifth Distillate | Fifth Residue | Sixth Distillate | Sixth Residue |
|---|---|---|---|---|---|---|---|---|---|---|---|---|---|---|
| Ethanol | 41.33 | 33.42 | 18.27 | 43.01 | 89.74 | 0.02 | 1.85 | 0.00 | 4.88 | 0.07 | 0.00 | 0.00 | 40.96 | 90.94 |
| Butanol | 30.31 | 2.25 | 1.16 | 32.43 | 0.01 | 62.26 | 48.45 | 82.24 | 47.70 | 0.00 | 99.85 | 0.05 | 0.00 | 0.01 |
| Water | 16.07 | 7.71 | 4.22 | 16.94 | 8.92 | 24.31 | 48.07 | 0.05 | 47.33 | 99.90 | 0.06 | 0.00 | 4.60 | 9.03 |

TABLE 9-continued

SIMULATED COMPOSITIONAL DATA FOR PROCESS STREAMS

| Comp. | Feed | First Distillate | Vent | First Residue | Second Distillate | Second Residue | Third Distillate | Third Residue | Fourth Distillate | Fourth Residue | Fifth Distillate | Fifth Residue | Sixth Distillate | Sixth Residue |
|---|---|---|---|---|---|---|---|---|---|---|---|---|---|---|
| Hexanol | 6.51 | 0.04 | 0.02 | 6.99 | 0.00 | 13.41 | 1.63 | 17.71 | 0.09 | 0.03 | 0.09 | 99.95 | 0.00 | 0.00 |
| DEE | 2.14 | 33.20 | 31.55 | 0.00 | 0.00 | 0.00 | 0.00 | 0.00 | 0.00 | 0.00 | 0.00 | 0.00 | 0.00 | 0.00 |
| Ethylene | 1.90 | 3.37 | 28.14 | 0.00 | 0.00 | 0.00 | 0.00 | 0.00 | 0.00 | 0.00 | 0.00 | 0.00 | 0.00 | 0.00 |
| AcH | 1.01 | 18.50 | 14.80 | 0.00 | 0.01 | 0.00 | 0.00 | 0.00 | 0.00 | 0.00 | 0.00 | 0.00 | 0.29 | 0.00 |
| BuH | 0.65 | 33.20 | 0.89 | 0.63 | 1.32 | 0.00 | 0.00 | 0.00 | 0.00 | 0.00 | 0.00 | 0.00 | 54.15 | 0.02 |

While the invention has been described in detail, modifications within the spirit and scope of the invention will be readily apparent to those of skill in the art. It should be understood that aspects of the invention and portions of various embodiments and various features recited above and/or in the appended claims may be combined or interchanged either in whole or in part. In the foregoing descriptions of the various embodiments, those embodiments which refer to another embodiment may be appropriately combined with other embodiments as will be appreciated by one of ordinary skill in the art. Furthermore, those of ordinary skill in the art will appreciate that the foregoing description is by way of example only, and is not intended to limit the invention.

We claim:

1. A process for producing multi-carbon alcohols, comprising the steps of:
    reacting ethanol in a reactor to form a crude product comprising butanol, ethanol, and water;
    separating at least a portion of the crude product in a first distillation zone to form a first distillate comprising ethanol and a first residue comprising butanol, and water; and
    separating at least a portion of the first residue in a second distillation zone to form a second distillate and a second residue comprising butanol.

2. The process of claim 1, further comprising the step of forming from the first residue a heterogeneous azeotrope comprising more than one liquid phase.

3. The process of claim 2, wherein the more than one liquid phase comprises an aqueous phase comprising greater than 50 wt. % water and less than 50 wt. % butanol; and/or an organic phase comprising greater than 50 wt. % butanol and less than 50 wt. % water.

4. The process of claim 1, wherein the first distillation zone comprises at least one column and the at least one column operates at a pressure above 10 psig and or at a temperature above 90° C.

5. The process of claim 1, wherein the second distillation zone comprises at least two distillation columns.

6. The process of claim 5, wherein each of the at least two distillation columns forms a distillate comprising from 30 wt. % to 70 wt. % butanol and from 30 wt. % to 70 wt. % water.

7. The process of claim 5, wherein the first of the at least two distillation columns operates at a top pressure lower than the top pressure of the second of the at least two distillation columns.

8. The process of claim 1, wherein the crude product further comprises hexanol.

9. The process of claim 1, wherein the crude product is substantially free of methanol, propanol, pentanol, or isotopes thereof and/or wherein the crude product is substantially free of esters of butanol, ethanol, hexanol, methanol, pentanol, or octanol.

10. The process of claim 1, wherein the crude product comprises
    from 0.1 wt. % to 60 wt. % ethanol;
    from 15 wt. % to 80 wt. % butanol;
    from 1 wt. % to 30 wt. % water; and
    from 0.1 wt. % to 30 wt. % hexanol.

11. The process of claim 1, wherein the crude product comprises, by weight, more ethanol than butanol.

12. The process of claim 1, wherein the crude product is fed to the first distillation zone as a liquid or as a mixture of liquid and vapor.

13. The process of claim 1, wherein the first distillate further comprises one or more light ends compound selected from the group consisting of acetaldehyde, ethylene, butyraldehyde, and diethyl ether.

14. The process of claim 13, further comprising the step of condensing at least a portion of the first distillate to form a condensed first distillate; and
    removing a vent stream comprising the one or more light ends compounds.

15. The process of claim 14, wherein the condensed first distillate comprises ethanol and wherein the process further comprises the step of:
    feeding to the reactor the condensed first distillate.

16. The process of claim 14, wherein the condensed first distillate comprises greater than 70 wt. % ethanol and/or from 0.001 wt. % to 2 wt. % butanol.

17. The process of claim 1, wherein the first residue comprises less than 0.5 wt. % ethanol.

18. The process of claim 1, wherein the first residue is substantially free of one or more light ends compounds selected from the group consisting of acetaldehyde, ethylene, butyraldehyde, and diethyl ether.

19. The process of claim 1, further comprising the step of separating at least a portion of the second residue in a third distillation zone to form a third distillate comprising butanol and a third residue comprising hexanol.

20. The process of claim 19, wherein the second residue comprises less than 1 wt. % water and/or wherein the third distillate comprises:
    from 95 wt. % to 99.99 wt. % butanol,
    from 0.01 to 3 wt. % hexanol, and
    from 0.01 wt. % to 1 wt. % water.

* * * * *